United States Patent [19]
Vora et al.

[11] Patent Number: 5,338,889
[45] Date of Patent: Aug. 16, 1994

[54] ALKANE REJECTION IN C$_4$ ETHERIFICATION AND ISOMERIZATION PROCESS

[75] Inventors: Bipin V. Vora, Darien; Tamotsu Imai, Mount Prospect; Peter J. Pujado, Palatine, all of Ill.

[73] Assignee: UOP, Des Plaines, Ill.

[21] Appl. No.: 998,169

[22] Filed: Dec. 29, 1992

[51] Int. Cl.$^5$ ............................................. C07C 41/06
[52] U.S. Cl. ...................................... 568/697; 585/324
[58] Field of Search .......................................... 568/697

[56] References Cited

U.S. PATENT DOCUMENTS

| | | | |
|---|---|---|---|
| 4,048,111 | 9/1977 | Rosback et al. | 502/79 |
| 4,440,871 | 4/1984 | Lok et al. | 502/214 |
| 4,503,282 | 3/1985 | Sikkenga | 585/671 |
| 4,581,474 | 4/1986 | Hutson et al. | 568/697 |
| 4,695,560 | 9/1987 | Gattuso et al. | 502/222 |
| 4,734,540 | 3/1988 | Gattuso et al. | 585/276 |
| 4,758,419 | 7/1988 | Lok et al. | 423/306 |
| 4,778,943 | 10/1988 | Sun | 585/671 |
| 4,814,517 | 3/1989 | Trubac | 568/697 |
| 4,814,519 | 3/1989 | Harandi et al. | 568/697 |
| 5,008,466 | 4/1991 | Schleppinghoff et al. | 568/697 |
| 5,157,178 | 10/1992 | Gajda et al. | 568/697 |
| 5,210,327 | 5/1993 | Luebke et al. | 568/697 |

*Primary Examiner*—Howard T. Mars
*Attorney, Agent, or Firm*—Thomas K. McBride; John G. Tolomei

[57] ABSTRACT

A combination of an etherification process and a process for the isomerization of linear alkenes to isoalkenes uses an adsorptive separation zone for olefin and paraffin separation upstream of the MTBE unit to reduce olefin losses associated with the rejection of butanes. The location of the MTBE unit downstream of the adsorptive separation zone facilitates the essentially complete removal of isobutane from the process. Supplemental rejection of isobutane downstream of the adsorptive separation permits the use of low purity adsorptive separation zone and also allows the recovery of a high purity butene-1 product.

5 Claims, 1 Drawing Sheet

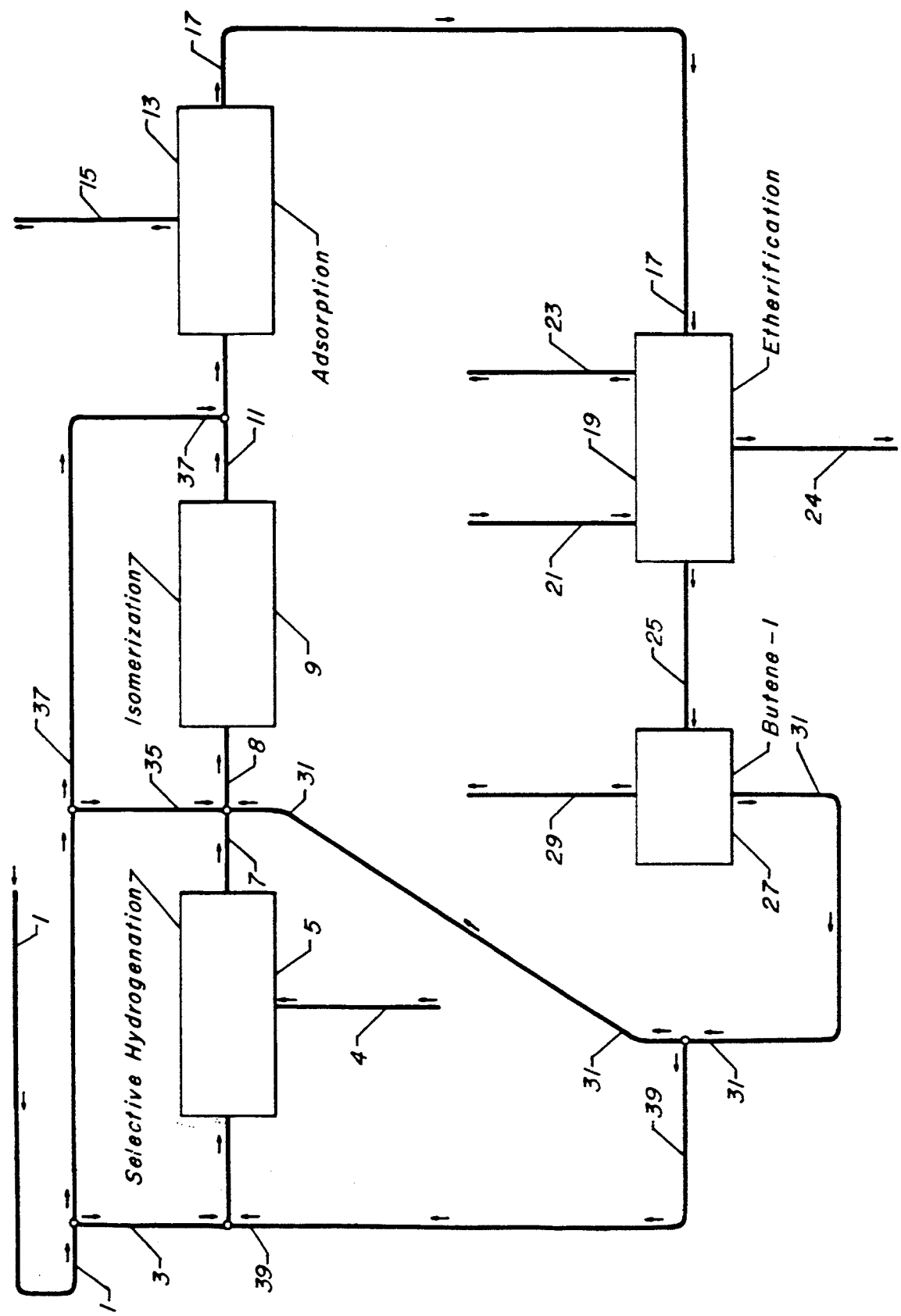

ALKANE REJECTION IN C₄ ETHERIFICATION AND ISOMERIZATION PROCESS

FIELD OF THE INVENTION

This invention relates to processes for the production of ethers by the reaction of an alcohol with an isoolefin. More specifically this invention relates to a process for the production of butyl ether and the skeletal isomerization of normal butene to provide additional feedstock for the production of ethers.

BACKGROUND OF THE INVENTION

The production of ethers by the reaction of an isoolefin and an alcohol are well known commercial operations. There are many detailed descriptions of processes for the production of such ethers, in particular, methyl tertiary butyl ether (MTBE) and methyl tertiary amyl ether (TAME). These ethers have long been known as useful octane blending agents for gasoline motor fuels due to their high octane number (RON) of about 120. More recently ether compounds as gasoline blending components have been highly valued as supplying oxygen to meet reformulated gasoline requirements. Processes for the production of MTBE and TAME by reacting methanol with isobutylene or isoamylene, respectfully, are among the most widely known processes for the production of such ethers.

Processes for the production of such ethers have suffered from a shortage of the necessary isoolefins for reaction with the alcohols to provide products. Feedstreams for etherification processes typically consist of a wide variety of olefinic and paraffinic isomers. It is known that the available feedstock can be increased by the isomerization and dehydrogenation of paraffins and the skeletal isomerization of olefins. Methods for the dehydrogenation of paraffins, in particular isoparaffins, are known in the art as are processes for the skeletal isomerization of normal olefins to isoolefins. Since many of the olefinic and paraffinic isomers of any given carbon number have relatively close boiling points, separation of the isomers in an efficient manner to enhance the production of ether as well as the conversion of unreacted products to additional reactants have been difficult. Methods for the various separations have included adsorptive separations as well as extractive distillations. Unreacted olefins and paraffins have also been used as feed to alkylation units. There is a need for etherification and isomerization process arrangements that simplify the separation of olefinic and paraffinic isomers to provide product and reactants.

Since the butane isomers are not converted in the etherification or isomerization zone various process steps and schemes have been proposed for the efficient rejection of the these paraffins. Again the close boiling points of the saturated and unsaturated isomers can lead to a problem of olefin loss by the carryover of these hydrocarbons with the usually vented paraffins. To prevent this carryover processes have employed high efficiency extractive distillation, adsorption, or other methods to separate the normal butenes from butane.

It is an object of this invention to provide a process arrangement for the rejection of butane from combination isomerization and etherification processes for the conversion of C₄ hydrocarbons.

It is a further object of this invention to provide a butyl ether product and a high purity butene-1 product in a simplified etherification and isomerization arrangement and without the use of extractive distillation.

SUMMARY OF THE INVENTION

It has been discovered that arranging isomerization of normal butenes, adsorptive separation of paraffins and etherification of isobutene in series and in this specific order will improve the effectiveness of rejecting normal butane and reduce the loss of olefin reactants. This arrangement rejects isobutane and normal butane with only a minor loss of valuable olefin isomers while also providing a butene fraction from that can supply a high purity butene-1 product.

Accordingly in one embodiment this invention is a process for the production of butyl ethers from a mixed C₄ feedstream comprising isobutane normal butane, normal butenes, and isobutene, and a monohydroxy alcohol. The process includes the steps of passing an isomerization zone feed stream to an isomerization reaction zone for the skeletal isomerization of normal butenes and contacting the isomerization zone feed with an isomerization catalyst at isomerization conditions to produce an isomerization zone effluent stream. An adsorption zone receives at least a portion of the isomerization zone effluent stream as an adsorption feed and therein contacts the adsorption feed with an adsorbent at adsorption conditions to separate the adsorption feed into a saturate stream comprising butane isomers and an etherification zone feed fraction comprising isobutene and normal butenes. At least a portion of the etherification zone feed fraction mixes with a $C_1$-$C_5$ monohydroxy alcohol to produce a combined feed. The combined feed contacts an etherification catalyst in an etherification zone at etherification conditions to react isobutene with the alcohol and produce an etherification effluent stream comprising alcohol, butyl ether, isobutane, and normal butene isomers. A separation zone input stream comprising at least a portion of the etherification effluent stream passes to a first separation zone that withdraws a high boiling first fraction comprising the ether from the separation zone, and a second fraction comprising alcohol, isobutane, and normal butene isomers and recovering alcohol from the second fraction in the first separation zone. An isomerization feed comprising at least a portion of the second fraction passes to the isomerization zone. The mixed C₄ feedstream enters either or both of the adsorption zone and the isomerization zone.

In a more limited embodiment this invention is a process for the production of butyl ethers from a mixed C₄ feedstream comprising butanes, normal butenes, isobutene, and butadiene, and a monohydroxy alcohol, the process comprising: passing the mixed C₄ feedstream to a selective hydrogenation zone and contacting the feed stream with a selective hydrogenation catalyst at selective hydrogenation conditions to saturate diolefins and produce a selectively hydrogenated effluent stream; passing the effluent stream from the selective hydrogenation zone to an isomerization reaction zone for the skeletal isomerization of normal butenes and contacting the isomerization zone feed with an isomerization catalyst at isomerization conditions to produce an isomerization zone effluent stream; passing at least a portion of the isomerization zone effluent stream directly to an adsorption zone as an adsorption feed, contacting the adsorption feed with an adsorbent at adsorption conditions to separate the adsorption feed into a saturate stream comprising at least a part of the butane isomers and an etherification zone feed fraction comprising isobutane, isobutene and normal butenes; mixing at least a portion of the etherification zone feed fraction with a $C_1$–$C_5$ monohydroxy alcohol to produce a combined feed and contacting the combined feed with an etherification catalyst in an etherification zone at etherification conditions to react isobutene with the alcohol and produce an etherification effluent stream comprising, alcohol, butyl ether, isobutane, normal butane and normal butene isomers; passing a separation zone input stream comprising the etherification effluent stream to a first separation zone, withdrawing a high boiling first fraction comprising the ether from the separation zone, separating light gases, isobutane, and alcohol from the remainder of the etherification zone effluent stream and withdrawing a second fraction comprising normal butane and normal butene isomers from the first separation zone; passing at least a portion of the second fraction to a second separation zone and separating the second fraction into a butene-1 product stream having a purity of at least 99.0% and a third fraction comprising normal butane and butene-2; passing an isomerization feed comprising at least a portion of the third fraction to the isomerization zone; and, passing a mixed $C_4$ feedstream into at least one of the selective hydrogenation zone, the adsorption zone and the isomerization zone.

Additional aspects of this invention relate to the arrangements required for distillation of feedstreams, reaction zone locations and treatment zones. Thus, for example, the order of the fractionation for the recovery of butene-1 may be reversed such that normal butane and butene-2 are first rejected as heavy components and the overhead product is further fractionated to separate isobutane and other light components overhead while butene-1 is recovered as a high purity bottoms product. The separation zone of this invention may also provide reactive distillation to enhance the conversion of product and the recovery of potential reactants. The following detailed description of the invention sets forth additional details, embodiments, and aspects of the invention.

BRIEF DESCRIPTION OF THE DRAWING

The FIGURE shows a schematic illustration of a process of this invention showing the etherification zone, isomerization zone, and adsorption zone, along with additional separators, and treating zones for the purification of the feedstream and product.

DETAILED DESCRIPTION OF THE INVENTION

This invention is broadly applicable to the production of butyl ethers. The advantages of this invention are achieved when the feedstream includes a mixture of normal and iso- butene and butane isomers. In an etherification process for the production of butyl ethers, the typical feedstream will consist of a mixture of $C_4$ isomers comprising isobutane, isobutene, normal butane, 1-butene and 2-butene. The mixed $C_4$ feed stream will often contain from 5 to 50 wt % butanes. Since in the combination of etherification and skeletal olefin isomerization processes, the alkanes are not reacted to any significant degree, these components increase the amount of material that passes through the process and must be removed to prevent an unacceptable build-up of unreacted products that circulate through the process. Although a variety of sources are available to provide such feedstreams, the most common source of the feedstreams for these processes are fight cracked hydrocarbon streams from an FCC unit, or a $C_4$ stream from a steam cracker after butadiene extraction.

Often these hydrocarbon streams will contain diolefins in addition to the desired monoolefin feed components. These diolefins interfere with the operation of the catalyst in downstream processes by polymerizing and forming heavy hydrocarbon compounds that block the active sites of the catalyst and prevent their use. Preferably, feedstreams for this process will undergo treatment for the elimination of diolefins. A common method of eliminating diolefins is by the selective hydrogenation of the diolefins to saturate the diolefins into monoolefins while preserving monoolefins. Those skilled in the art know a variety of selective hydrogenation processes for the saturation of diolefins to monoolefins. A particular catalyst and operating conditions for such selective hydrogenation processes can be found in U.S. Pat. Nos. 4,695,560 and 4,734,540 the contents of which are hereby incorporated by reference. The selective hydrogenation process typically employs a nickel on aluminum catalyst or a noble metal, such as palladium on alumina, for the selective hydrogenation. The nickel and/or palladium may be sulfided or unsulfided. The process can also operate at a broad range of operating conditions including pressures of from 40 to 800 psig with pressures of between 50 and 300 psig being preferred and temperatures of from °–700° F. with temperatures of from about 120°–400° F. being preferred. Effective space velocities for the processes should be above 1 $hr^{-1}$ and preferably are above 5 with a range of from between 5 to 35 $hrs^{-1}$. It is typical in such processes to limit the amount of hydrogen to prevent the saturation of monoolefins such that there is less than 2 times the stoichiometric amount of hydrogen required for the selective hydrogenation in the process. Preferably, the mol ratio of hydrogen to diolefinic hydrocarbons in the material will be in a range of from 1:1 to 1.8:1, and in some cases the hydrogen will be less than the stoichiometrically required amount of hydrogen. Additional information related to the selective hydrogenation of diolefinic hydrocarbons can be found in U.S. Pat. No. 4,695,560.

The selective hydrogenation process can be located at any location within the process loop. Preferably the feed to the selective hydrogenation zone directly provides the feed to the isomerization zone. Having the selective hydrogenation provide the feed to isomerization simplifies the delivery of hydrogen to the selective hydrogenation and, if necessary, the isomerization zone.

Whether or not the process includes selective hydrogenation, normal butenes in the process loop undergo skeletal isomerization to produce additional isobutene for the etherification process. In order to maintain catalyst stability in the isomerization zone the streams entering the isomerization zone often requires removal of polar contaminants such as sulfur, nitrogen or oxygen compounds. Thus, in addition to any selective hydrogenation the incoming stream to the isomerization zone may also require additional purification for the removal of compounds that can poison the catalyst or interfere with the skeletal isomerization process. Depending on the type of catalyst used for the skeletal isomerization of olefins, compounds that are usually most harmful to the isomerization catalyst include water, oxygenated compounds and nitrogen compounds. A variety of methods are known to remove such compounds which include water washing, adsorption and extraction processes. Oxygenated compounds and nitrogen compounds can be removed by typical adsorbents for the removal of these contaminants comprised zeolitic molecular sieves. Suitable types of zeolites are faujasites having pore sizes of about 10 angstroms. In particular, such zeolites include X, Y and L types as described in U.S. Pat. Nos. 3,216,789; 2,882,244 and 3,130,007. A particularly preferred type of zeolite is 13X. The use of type 13X sieves for the removal of oxygenate compounds such as dimethyl ethers from the effluent from an etherification process is described in U.S. Pat. No. 4,814,517, the contents of which are hereby incorporated by reference. Suitable operation of the isomerization zone will require the removal of water and oxygenate compounds to a level of less than 50 wppm, and preferably less than 5 wppm water equivalents. Common nitrogen and oxygenate compounds that have also been found in light cracked products from an FCC unit include acetone and acetonitrile. These compounds are preferably removed by water washing such feeds prior to introduction into the process.

The normal butene rich input stream after any necessary purification enters the isomerization zone. (The term rich when used herein means a stream having a weight or volume percent content of at least 30% of the mentioned component while the term relatively rich means a stream having a higher concentration of the mentioned component than the feed from which it was derived.) In the production of MTBE the isomerization zone will preferably contain at least 30 wt % butane. Having a saturate concentration of between 30 to 80 wt % in the feed is believed to offer benefits of reduced coking.

Methods for converting the normal butene components to isobutene components by isomerization are known in the art. A process for converting linear alkenes to isomerized alkenes using a crystalline or silicate molecular sieve is taught in U.S. Pat. No. 4,503,282. Additional catalyst and methods for the skeletal isomerization of linear alkenes are described in U.S. Pat. No. 4,778,943 and 4,814,519. A preferred catalyst for the isomerization reaction zone of this invention is a nonzeolitic molecular sieve. Preferred forms of the nonzeolitic molecular sieve for this invention includes silicoaluminophosphates and a magnesium aluminophosphate. Suitable non-zeolitic catalysts such as the SAPO and MgAPSO are described in U.S. Pat. No. 4,440,871 and 4,758,419 which are hereby incorporated by reference. The catalyst for the isomerization zone typically lies in a fixed bed arrangement. In order to permit in-situ regeneration, the isomerization zone may include multiple reactors in a swing bed arrangement. Preferably, the reactants contact the catalyst in a vapor phase flow. Contacting a linear alkene feed with a catalyst in the presence of hydrogen in a molar ratio of from about 0.01 to 9, and preferably in a ratio of from 0.03 to 4, aids the process by suppressing the formation of carbon compounds on the catalyst. The isomerization process will typically operate over a broad range of conditions including temperatures of from 120°–1300° F. with temperatures in the range of 200°–1000° F. being preferred. Pressures for the isomerization reaction will also vary over a wide range extending from vacuum conditions to 700 psig, and preferably are in a range of 50 to 350 psig. Space velocities can also vary over a wide range from 0.5 to 100 hr$^{-1}$ with a preferred range of 1-5 hr$^{-1}$. The expected per pass conversion of normal alkenes to isoalkenes in the isomerization zone will generally reach at least 30% of the total combined feed entering the reaction zone and will more typically exceed 40%.

The effluent stream from the isomerization zone containing isoalkenes normally undergoes separation for the recovery of light gases including hydrogen. Hydrogen recovered in the light gases from the isomerization zone is recycled to the inlet of the isomerization zone to provide any necessary hydrogen concentration. The effluent from the isomerization zone may also undergo additional separation to remove additional light ends or reject heavier by-product hydrocarbons. Heavy materials such as $C_6^+$ olefinic hydrocarbons tend to foul or deactivate the etherification catalyst.

The isomerization zone may also operate without the separation of light ends for the recovery of hydrogen. In one embodiment of this invention the isomerization zone may operate with no hydrogen addition or with once-through hydrogen addition which only adds hydrogen up to about the solubility limits of the isomerization feed. For once-through operations the feed to the isomerization zone will usually have a hydrogen to hydrocarbon ratio of 0.01 to 0.05. A particularly preferred arrangement of this invention includes the selective hydrogenation reactor to saturate diolefins and the effluent from the selective hydrogenation zone is fed directly to the olefin isomerization reactor without intermediate separation to supply the hydrogen for the requirements of the olefin isomerization.

Following isomerization at least a portion of the butane and butene containing stream passes through a selective adsorption zone for the removal of a portion of the butane isomers. The adsorptive separation zone can use any adsorbent and bed operating arrangement that will selectively adsorb the saturated or unsaturated isomers in a continuous system and provide high purity saturated hydrocarbon fraction containing less than 10 wt % olefins and an unsaturated stream comprising isobutene and normal butenes. Suitable methods for the selective adsorption include swing bed systems and simulated moving bed system. Particular arrangements for moving bed systems are disclosed in U.S. Pat. No. 2,985,589 issued to Broughton, and U.S. Pat. No. 4,402,832 issued to Gerhold the contents of which are herein incorporated by reference.

A number of adsorbents are known for separating olefins from saturated hydrocarbons. Appropriate adsorbents are described in the above listed patents. Sodium exchanged X and Y type zeolites are known to be particularly useful adsorbents in the separation of olefins from paraffinic hydrocarbons. Particular methods of treating type X and Y zeolites to improve olefin selectivity and reduce undesired cracking reactions are taught in U.S. Pat. No. 4,048,111 the teachings of which are herein incorporated by reference.

Although both liquid and vapor phase operations can be used in many adsorptive type separation processes, liquid-phase operation is preferred for this process because of the lower temperature requirements and because of the higher yields of adsorbed material or extract that can be obtained with liquid-phase operation over those obtained with vapor-phase operation. Adsorption conditions will, therefore, include a pressure sufficient to maintain liquid phase. Temperatures for the adsorption step of the separation will usually range from ambient to about 300° F. and pressure will range from atmospheric to 500 psig. Desorption conditions will generally include the same range of temperatures and pressures as used for extract conditions.

This process is especially suited for adsorption systems that use multiple beds for supplying the process streams to the adsorbent and divide the adsorbent into a plurality of zones for adsorbing olefins, recovering paraffins, purifying the adsorbent, and desorbing the olefins. A well-known process of this type is the simulated countercurrent moving bed system for simulating moving bed countercurrent flow systems and is generally taught in U.S. Pat. No. 3,510,423, the contents of which are hereby incorporated by reference. Such systems have a much greater separation efficiency than fixed molecular sieve bed systems. In the moving bed or simulated moving bed processes, the retention and displacement operations are continuously taking place which allows both continuous production of an extract and a raffinate stream and the continual use of feed and desorbent streams. In such a system it is the progressive movement of multiple liquid access points down a molecular sieve chamber that simulates the upward movement of molecular sieve contained in the chamber.

A number of specially defined terms are used in describing the simulated moving bed processes. The term "feed stream" indicates a stream in the process through which feed material passes to the molecular sieve. A feed material comprises one or more extract components and one or more raffinate components. An "extract component" is a compound or type of compound that is more selectively retained by the molecular sieve while a "raffinate component" is a compound or type of compound that is less selectively retained. In the preferred separation zone of this invention olefinic hydrocarbons from the feed stream are extract components while feed stream saturated or paraffinic components are raffinate components. The term "extract component" as used herein refers to a more selectively retained compound such as olefinic hydrocarbons in this process. The term "displacement fluid" "or desorbent" shall mean generally a material capable of displacing an extract component. The term "desorbent" or "desorbent input stream" indicates the stream through which desorbent passes to the molecular sieve. The term "raffinate output stream" means a stream through which most of the raffinate components are removed from the molecular sieve. The composition of the raffinate stream can vary from about 100% desorbent to essentially 100% raffinate components. The term "extract stream" or "extract output stream" means a stream through which an extract material which has been displaced by a desorbent is removed from the molecular sieve. The composition of the extract stream can also vary from about 100% desorbent to essentially 100% extract components.

The term "selective pore volume" of the molecular sieve is defined as the volume of the molecular sieve which selectively retains extract components from the feedstock. The term "non-selective void volume" of the molecular sieve is the volume of the molecular sieve which does not selectively retain extract components from the feedstock. This non-selective void volume includes the cavities of the molecular sieve which are not capable of retaining extract components and the interstitial void spaces between molecular sieve particles. The selective pore volume and the non-selective void volume are generally expressed in volumetric quantities and are of importance in determining the proper flow rates of fluid required to be passed into an operational zone for efficient operations to take place for a given quantity of molecular sieve.

When molecular sieve "passes" into an operational zone (hereinafter defined and described) its non-selective void volume together with its selective pore volume carries fluid into that zone. The non-selective void volume is utilized in determining the amount of fluid which should pass into the same zone in a countercurrent direction to the molecular sieve to displace the fluid present in the non-selective void volume. If the fluid flow rate passing into a zone is smaller than the non-selective void volume rate of molecular sieve material passing into that zone, there is a net entrainment of liquid into the zone by the molecular sieve. Since this net entrainment is a fluid present in non-selective void volume of the molecular sieve, it, in most instances, comprises less selectively retained feed components.

In the preferred simulated moving bed process only four of the access lines are active at any one time: the feed input stream, displacement or desorbent fluid inlet stream, raffinate outlet stream, and extract outlet stream access lines. Coincident with this simulated upward movement of the solid molecular sieve is the movement of the liquid occupying the void volume of the packed bed of molecular sieve. So that countercurrent contact is maintained, a liquid flow down the molecular sieve chamber may be provided by a pump. As an active liquid access point moves through a cycle, that is, from the top of the chamber to the bottom, the chamber circulation pump moves liquid through different zones which require different flow rates. A programmed flow controller may be provided to set and regulate these flow rates.

The active liquid access points effectively divide the molecular sieve chamber into separate zones, each of which has a different function. In this embodiment of the process, it is generally necessary that three separate operational zones be present in order for the process to take place although in some instances an optional fourth zone may be used.

The retention or extract zone, zone 1, is defined as the molecular sieve located between the feed inlet stream and the raffinate outlet stream. In this zone, the feedstock contacts the molecular sieve, an extract component is retained, and a raffinate stream is withdrawn. Since the general flow through zone 1 is from the feed stream which passes into the zone to the raffinate stream which passes out of the zone, the flow in this zone is considered to be a downstream direction when proceeding from the feed inlet to the raffinate outlet streams.

Immediately upstream with respect to fluid flow in zone 1 is the purification zone, zone 2. The purification zone is defined as the molecular sieve between the extract outlet stream and the feed inlet stream. The basic operations taking place in zone 2 are the displacement from the non-selective void volume of the molecular sieve of any raffinate material carried into zone 2 by the shifting of molecular sieve into this zone and the displacement of any raffinate material retained within the selective pore volume of the molecular sieve. Purification is achieved by passing a portion of extract stream material leaving zone 3 into zone 2 at zone 2's upstream boundary to effect the displacement of raffinate material. The flow of material in zone 2 is in a downstream direction from the extract outlet stream to the feed inlet stream.

Immediately upstream of zone 2 with respect to the fluid flowing in zone 2 is the displacement or desorption zone, zone 3. The desorption zone is defined as the molecular sieve between the desorption inlet and the extract outlet stream. The function of the desorption zone is to allow a desorbent which passes into this zone to displace the extract component which was retained in the molecular sieve during a previous contact with feed in zone 1 in a prior cycle of operation. The flow of fluid in zone 3 is essentially in the same direction as that of zones 1 and 2.

In some instances, an optional buffer zone, zone 4, has been utilized. This zone, defined as the molecular sieve between the raffinate outlet stream and the desorbent inlet stream, if used, is located immediately upstream with respect to the fluid flow to zone 3. Since this invention preferably operates at a low efficiency to maintain paraffins in the extract stream Zone 4 is not usually necessary. Therefore, the raffinate stream passed from zone 1 to zone 3 does not need careful monitoring since an appreciable quantity of raffinate material can contaminate the extract stream.

A cyclic advancement of the input and output streams through the fixed bed of molecular sieve can be accomplished by utilizing a manifold system in which the valves in the manifold are operated in a sequential manner to effect the shifting of the input and output streams thereby allowing a flow of fluid with respect to solid molecular sieve in a countercurrent manner. Another mode of operation which can effect the countercurrent flow of solid molecular sieve with respect to fluid involves the use of a rotating disc valve in which the input and output streams are connected to the valve and the lines through which feed input, extract output, displacement fluid input and raffinate output streams pass are advanced in the same direction through the molecular sieve bed. Both the manifold arrangement and disc valve are known in the art. Specifically rotary disc valves which can be utilized in this operation can be found in U.S. Pat. Nos. 3,040,777 and 3,422,848, incorporated herein by reference. Both of the aforementioned patents disclose a rotary type connection valve in which the suitable advancement of the various input and output streams from fixed sources can be achieved without difficulty.

In liquid phase adsorption systems the adsorbent contains selective pores that will more strongly adsorb the selectively adsorbed components in the feed mixture. Most moving bed adsorption processes use a desorbent material that has a different composition than the primary components in the feed stream to the adsorption section to displace extract materials from the selective pore volume. As a result the desorbent material is typically recovered from the material that it has desorbed for reuse in the adsorption section. It has been the usual practice to use a raffinate column to separate the desorbent material from the raffinate stream. The desorbent material is also a selectively adsorbed component. The selective pore volume is limited and the quantity of such pores must accommodate the desired volume of components to be adsorbed from the feed mixture. Therefore, an extract column is typically used to recover desorbent, otherwise desorbent material will be lost or may build up in the separation cycle increasing the amount of adsorbed component in the feed mixture and requiring additional adsorbent.

A useful desorbent for the typical feedstream of this invention will comprise a saturated and unsaturated mixture of aliphatic hydrocarbons having a higher carbon number than the feed stream hydrocarbons. The higher carbon number desorbents are readily separated from the separated feedstream components. For butene and butane separation a preferred desorbent mixture comprises a mixture of normal hexane and normal hexene. Preferably the mixture comprises 30 to 70% hexenes.

By-passing a portion of the butene and butane stream around the adsorptive separation zone can provide further adjustments in the relative olefin to paraffin concentration of the feed stream to the isomerization zone. Where the paraffin concentration of the feedstream is low, only a relatively small portion of the isomerization effluent need pass through the adsorptive separation zone for paraffin removal. The concentration of the paraffins maintained in the isomerization zone feed is preferably in a range of from 20 to 50 wt %. Thus the amount of unreacted isomerization effluent entering the adsorptive separation zone can typically vary from 10 to 100 vol % of the feed that enters the etherification zone.

The feed to the etherification zone includes an alcohol to react with the isoolefin and produce the desired ether product. The alcohols that can be used are typically $C_1$–$C_5$ monohydroxy alcohols. Methanol typically constitutes the alcohol of choice for the etherification process. Ethanol, although used less commonly, is also a commonly available alcohol for the etherification process. Methanol is preferred somewhat since it is a stable commercial chemical of long standing.

At minimum isobutene as well as normal butene hydrocarbons will enter the etherification zone along with the alcohol. Preferably the feed fraction entering the etherification zone will contain at least 5 vol % isobutane. More typically the hydrocarbons entering the etherification zone will include isobutane and butane. Contact with the etherification catalyst at etherification conditions will produce the butyl ether product. A wide range of materials are known to be effective as etherification catalysts for the isobutene reactant including mineral acids such as sulfuric acid, boron trifluoride, phosphoric acid on kieselguhr, phosphorus-modified zeolites, heteropoly acids, and various sulfonated resins. The use of a sulfonated solid resin catalyst is preferred. These resin type catalysts include the reaction products of phenolformaldehyde resins and sulfuric acid and sulfonated polystyrene resins including those crosslinked with divinylbenzene. A particularly preferred etherification catalyst is a macroporous acid form sulfonic ion exchange resin such as a sulfonated styrene-divinylbenzene resin as described in U.S. Pat. No. 2,922,822 having a degree of crosslinking of from about 5 to 60%. Suitable resins are available commercially. Specialized resins have been described in the an and include copolymers of sulfonyl fluorovinyl ether and fluorocarbons as described in U.S. Pat. No. 3,849,243. Another specially prepared resin consists of the $SiO_2$ modified cation exchangers described in U.S. Pat. No. 4,751,343. The macroporous structure of a suitable resin is described in detail in U.S. Pat. No. 5,012,031 as having a surface area of at least 400 $m^2/g$, a pore volume of 0.6–2.5 ml/g and a mean pore diameter of 40–1000 angstroms. It is contemplated that the subject process could be performed using a metal-containing resin which contains one or more metals from sub-groups VI, VII or VIII of the Periodic Table such as chromium, tungsten, palladium, nickel, chromium, platinum, or iron as described in U.S. Pat. No. 4,330,679. Further information on suitable etherification catalysts may be obtained by reference to U.S. Pat. Nos. 2,480,940, 2,922,822, and 4,270,929 and the previously cited etherification references.

A wide range of operating conditions are employed in processes for producing ethers from olefins and alcohols. Many of these include vapor, liquid or mixed phase operations. Processes operating with vapor or mixed phase conditions may be suitably employed in this invention. The preferred etherification process uses liquid phase conditions.

The range of etherification conditions for processes operating in liquid phase still includes a broad range of suitable conditions including a superatmospheric pressure sufficient to maintain the reactants as a liquid phase, generally below about 700 psig, and a temperature between about 85 and about 210° F. Even in the presence of additional light materials, pressures in the range of 140 to 580 psig are sufficient. A preferred temperature range is from 100°-210° F. The reaction rate is normally faster at higher temperatures but conversion is more complete at lower temperatures due to favorable thermodynamic equilibrium. High conversion in a moderate volume reaction zone can, therefore, be obtained if the initial section of the reaction zone, e.g., the first two-thirds, is maintained above 160° F. and the remainder of the reaction zone is maintained below 120° F. This may be accomplished most easily with two reactors. The ratio of feed alcohol to isoolefin should normally be maintained in the broad range of 1:1 to 2:1. With the isobutene reactant, good results are achieved if the ratio of methanol to isobutene is between 1.05:1 and 1.5:1. An excess of methanol, above that required to achieve satisfactory conversion at good selectivity, should be avoided as some decomposition of methanol to dimethyl ether may occur which may increase the load on separation facilities. Various etherification process techniques, reaction conditions and product recovery methods are described in U.S. Pat. Nos. 4,219,678 to Obenaus et al. and 4,282,389 to Droste et al. which are incorporated herein by reference.

The etherification zone operates selectively to principally convert only the isobutene. Etherification zones normally obtain high isobutene conversion which will typically exceed 98%. Alkanes and normal alkenes pass through the etherification zone without any significant conversion to products or by-products. Thus, the etherification zone effluent, together with the unreacted feed components, provides a stream of ether product, normal alkenes and normal and branched alkane isomers for separation. In most cases, the stream entering the separation zone will also contain unreacted alcohol. The separation zone receiving the ether products, alcohol and unreacted butane distills the product into three separate boiling point fractions. Similar to most separation systems for recovery of ethers, the product separation zone provides a high boiling fraction that principally contains ether product. The product separation zone of this invention separates alcohol from the remaining lower boiling components. Those skilled in the art are familiar with the various azeotropes formed by the ether products and alcohol and can provide suitable means for such separations and recoveries. As anticipated for most cases, methanol will be the usual alcohol and the low boiling point fraction will undergo an alcohol recovery step such as water washing. Alcohol recovery provides a low boiling fraction containing at least isobutane and normal butenes that were not reacted in the etherification process or enter the separation zone directly as part of the process feed. Isobutane comprises the lowest boiling constituent of the $C_4$ isomers. The isobutane can be conveniently withdrawn as a low boiling fraction from the separation zone such that the loss of valuable butene hydrocarbons is minimized.

The low concentration or elimination of isobutene from the recycle effluent of the etherification facilitates the recovery of butene-1. The absence of isobutane, isobutene, and butadiene, makes butene-1 the lowest boiling isomer with a boiling point about 10° F. lower than the next lowest boiling isomer that is present in substantial quantities. Therefore, addition of a relatively simple distillation column will provide a high purity butene-1 product. Preferably the butene-1 product produced by this invention will have a purity of at least 99.0 wt % and more preferably of at least 99.5 wt %.

In a continuously circulating process of this invention, normal butane is usually present in the process loop. The adsorption zone typically provides the sole path for rejecting the butane out of the process loop to prevent its build-up. Withdrawal of the normal butane by the adsorption zone establishes an equilibrium concentration of normal butane in the process loop.

Preferably, the feedstream of butane and butene isomers will enter the process at a point in the process loop just ahead of the isomerization zone. However, this feedstream may be added at a number of different points, depending on its composition, within this process loop. For example, it is also possible to add the feedstream at a point just ahead of the adsorptive separation zone or directly ahead of the etherification zone. The etherification zone may also precede the adsorption zone, depending on the relative feed compositions. In this way the total flow of reactants through the isomerization zone is reduced by eliminating reacted isobutene and rejected butane. Those skilled in the art are aware of the particular characteristics of the feedstream and the desired product streams that will dictate the most advantageous location for introducing the feedstream.

This invention is further described by reference to the FIGURE. In the FIGURE a feed comprising a $C_4$ fraction enters the process through line 1 and passes through a water wash zone (not shown) for the removal of soluble nitrogen compounds and light oxygenates from the feed. Purified feed via a line 3 and hydrogen via a line 4 passes to a selective hydrogenation zone 5 for the removal of trace diolefin compounds. Lines 7 and 8 pass the treated feed to an isomerization zone 9. The treated feed may be combined with a hydrogen recycle stream (not shown) in the isomerization reaction zone 9 to produce a combined isomerization zone feed for the skeletal isomerization of normal butenes to isobutene. The combined isomerization feed enters the isomerization reaction zone. The feed contacts a silicoaluminophosphate catalyst of the SAPO-11 type within the reaction zone. Line 11 withdraws the product effluent from the isomerization zone after it passes through a liquid vapor separation zone (not shown) for the recovery of the aforementioned optional hydrogen rich recycle stream.

Line 11 transfers the isomerization zone effluent to an adsorption zone 13. Adsorption feed taken by line 11 enters a simulated moving bed adsorptive separation zone in adsorption zone 13. Adsorptive separation zone 13 contacts the feed mixture with an adsorbent at a temperature of about 180° F. in a four zone simulated moving bed adsorption system. The system cycles through eight of more separate beds that contain the adsorbent in a cycle time of about 20 minutes. A desorbent consisting of a mixture of normal hexane and hexene desorbs the adsorbed olefins to provide an extract column product having a purity of about 80% at a recovery rate of about 87% which is recovered by a line 17 having the composition given in the Table. A line 15 rejects the paraffin rich raffinate from the process.

Methanol from a line 21 combines with the extract column product carried by line 17 in an etherification zone 19. Etherification reaction zone 19 contacts the combined feed with a sulfonated solid resin catalyst at a temperature of about 170° F. and a pressure of about 88 psig. Catalyst in etherification reaction zone 19 is arranged as a solid bed. Etherification reaction zone 19 contains a separation section (not shown) that recovers alcohol for the recycle to the etherification reactor, separates an MTBE product withdrawn by line 23, rejects a light ends stream containing isobutane via a line 24, and discharges a recycle stream 25.

Line 25 transports the recycle stream to a separator 27. Separator 27 recovers a butene-1 product stream having a purity of at least 99.0 wt %. A bottoms stream 31 carries the remainder of the recycle stream into admixture with the isomerization zone feed carried by line 8.

In addition the FIGURE also presents alternate locations for the feedstream addition and return of the recycle stream. For example where the diolefin concentration of the incoming feed is low, entering feed may bypass the selective hydrogenation zone and enter the isomerization directly via line 35. If both the diolefin concentration and the normal butene concentration are low, the incoming feed may also bypass the isomerization zone and enter the process directly via the adsorption zone through line 37 or optionally directly enter the etherification zone. When the feed initially bypasses the selective hydrogenation zone, the recycle stream may first pass by a line 39 to the selective hydrogenation zone before entering the isomerization zone. If the recovery of butene-1 is not desired, both separator 27 and the rejection of isobutane in the etherification zone may be eliminated. The adsorption zone will reject both isobutane and normal butane so as to establish the desired equilibrium concentration of saturates in the recycle loop.

What is claimed is:

1. A process for the production of methyl tertiary butyl ether MTBE from a mixed $C_4$ feedstream comprising butanes, normal butenes, and isobutene, and a monohydroxy alcohol, said process comprising:

(a) passing a selective hydrogenation zone feed stream to a selective hydrogenation zone and contacting said selective hydrogenation zone feed stream with a selective hydrogenation catalyst at selective hydrogenation conditions to saturate diolefins and produce a selectively hydrogenated effluent stream;

(b) passing said selectively hydrogenated effluent stream to an isomerization reaction zone as an isomerization zone feed for the skeletal isomerization of normal butenes and contacting said isomerization zone feed with an isomerization catalyst at isomerization conditions to produce an isomerization zone effluent stream;

(c) passing at least a portion of said isomerization zone effluent stream directly to an adsorption zone as an adsorption feed, contacting said adsorption feed with an adsorbent at adsorption conditions to separate said adsorption feed into a saturate stream comprising butane isomers and an etherification zone feed fraction comprising butane isomers, isobutene and normal butenes;

(d) mixing at least a portion of said etherification zone feed fraction with a $C_1$-$C_5$ monohydroxy alcohol to produce a combined feed and contacting said combined feed with an etherification catalyst in an etherification zone at etherification conditions to react isobutene with said alcohol and producing an etherification effluent stream comprising, alcohol, MTBE, isobutane, and normal butene isomers;

(e) passing a separation zone input stream comprising said etherification effluent stream to a first separation zone, withdrawing a high boiling first fraction comprising said MTBE from said separation zone, separating light gases, isobutane, and alcohol from the remainder of said etherification zone effluent stream and withdrawing a second fraction comprising normal butene isomers from separation zone;

(f) passing at least a portion of said second fraction to a second separation zone and separating said second fraction into a butene-1 product stream having a purity of at least 99 wt % and third fraction comprising normal butane and butene-2;

(g) passing at least a portion of said third fraction to said isomerization zone; and, (h) passing a mixed $C_4$ feedstream into at least one of said selective hydrogenation zone, said adsorption zone, and said isomerization zone.

2. The process of claim 1 wherein said etherification zone feed fraction contains at least 5 vol % isobutane.

3. The process of claim 1 wherein said feed stream passes first into said selective hydrogenation zone.

4. The process of claim 1 wherein said mixed $C_4$ feedstream contains from 5 to 50 wt % butane.

5. The process of claim 1 wherein said adsorbent selectively adsorbs normal butenes and isobutene.

* * * * *